(12) United States Patent
Loftus

(10) Patent No.: US 7,070,923 B1
(45) Date of Patent: Jul. 4, 2006

(54) PROVISION OF CARBON NANOTUBE BUCKY PAPER CAGES FOR IMMUNE SHIELDING OF CELLS, TISSUES, AND MEDICAL DEVICES

(75) Inventor: David J. Loftus, Palo Alto, CA (US)

(73) Assignee: The United States of America as represented by the Administrator of the National Aeronautics and Space Administration (NASA), Washington, DC (US)

( * ) Notice: Subject to any disclaimer, the term of this patent is extended or adjusted under 35 U.S.C. 154(b) by 86 days.

(21) Appl. No.: 10/608,884

(22) Filed: Jun. 26, 2003

(51) Int. Cl.
*C12Q 1/00* (2006.01)
(52) U.S. Cl. .................. 435/4; 435/6; 436/2; 436/518
(58) Field of Classification Search .................. 435/4, 435/6; 436/518, 2
See application file for complete search history.

*Primary Examiner*—James Ketter
(74) *Attorney, Agent, or Firm*—John F. Schipper; Robert M. Padilla

(57) ABSTRACT

System and method for enclosing cells and/or tissue, for purposes of growth, cell differentiation, suppression of cell differentiation, biological processing and/or transplantation of cells and tissues (biological inserts), and for secretion, sensing and monitoring of selected chemical substancesand activation of gene expression of biological inserts implanted into a human body. Selected cells and/or tissue are enveloped in a "cage" that is primarily carbon nanotube Bucky paper, with a selected thickness and porosity. Optionally, selected functional groups, proteins and/or peptides are attached to the carbon nanotube cage, or included within the cage, to enhance the growth and/or differentiation of the cells and/or tissue, to select for certain cellular sub-populations, to optimize certain functions of the cells and/or tissue and/or to optimize the passage of chemicals across the cage surface(s). A cage system is also used as an immuns shield and to control operation of a nano-device or macroscopic device, located within the cage, to provide or transform a selected chemical and/or a selected signal.

42 Claims, 4 Drawing Sheets

PROVISION OF CARBON NANOTUBE BUCKY PAPER CAGES FOR IMMUNE SHIELDING OF CELLS, TISSUES, AND MEDICAL DEVICES

STATEMENT REGARDING FEDERALLY SPONSORED REASEACH AND DEVELOPMENT

This invention was made by an employee of the federal government The U.S. Government has rights in this application.

CROSS REFERENCE TO RELATED APPLICATIONS (Not Applicable)

INCORPORATION BY REFERENCE OF MATERIAL SUBMITTED ON A COMPACT DISK (Not Applicable)

BACKGROUND OF THE INVENTION

1. Field of the Invention

This invention relates to fabrication and use of carbon nanotube Bucky paper "cages" for immune shielding of cells and tissues, for transplantation and other activities.

2. Description of the Related Art

Transplantation of cells and tissues from one human to another is limited by the host immune system, which identifies and rejects non-host cells and tissues with high efficiency. One strategy for avoiding or surmounting this barrier is to enclose the cells in a "cage" that provides a biological shield (an "immune shield") that, it is hoped, will prevent the transplanted cells and tissues from being rejected by the host immune system. This strategy would have application in endocrinology (e.g., islet cell transplantation), gene therapy (transplantation of cells to provide a missing protein or to replace a dysfunctional protein), immune therapy, or other biological therapy (transplantation of cells to provide specific immunoglobulins, cytokines, immune regulators or biological response modifiers). Such a system could also provide a micro-environment, within a human or other host body, for tissue engineering, to allow for differentiation of cells or assembly of tissue structures with two-dimensional or three-dimensional architecture or the formation of nascent organs, for subsequent use in the host or elsewhere.

Immune shielding may also serve as an important strategy for preventing immune rejection of implantable medical devices that range in size from ultra-small scale nanoparticles and nanoprobes to large scale macroscopic devices. The strategy of immune shielding allows use of a wider range of materials in the construction of implantable medical devices than would otherwise be possible because of the presence of the host immune system.

Many materials have been proposed as immune shields, including specially treated biological and non-biological materials, silicon, ceramics, synthetic polymers and other non-organic materials. As a rule, these foreign materials tend to provoke an immune response in the host body, and this has limited development in this field. Another phenomenon associated with transplantation of foreign materials into a host is localized scar formation and/or obstruction of pores in the foreign material. The presence of pores is required in most biological applications for efficient transfer of nutrients and other biological factors into the interior of the cage, and efficient transfer of waste products, metabolites and secreted substances from inside the cage to outside the cage.

What is needed is a biocompatible material that can be formed into a "cage" or similar structure for containing cells or tissue that prevents or limits access by the host immune system to the foreign cells or tissue. The cage material should allow the cells and/or tissue to be maintained in a live and functioning state; and in some cases, should permit the cells and/or tissue to carry out normal (physiological) and specially engineered sensing functions and/or normal (physiological) or specially engineered secretory functions. The cage material itself should not provoke (or should limit significantly) an immune response in the host system. The cage material itself should not elicit (or should limit significantly) scar formation in the host that, together with an immune response, could lead to obstruction of the pores of the cage material. The cage material itself should resist protein deposition that, together with scar formation or an immune response, could lead to obstruction of the pores. Preferably, the material should be flexible and sufficiently resilient to withstand the forces that may be involved in surgical implantation or transplantation and other forces that may be present in the host environment. The material should be configurable into a variety of geometric shapes, to optimize transport of substances across the cage and to promote the maintenance of cells and/or tissues.

BRIEF SUMMARY OF THE INVENTION

These needs are met by the invention, which provides construction of one or more cages, envelopes, enclosures or receptacles (referred to collectively herein as a "cage"), made primarily of carbon nanotube Bucky paper ("CNTBP") that have a selected degree of porosity, or "leakiness," to accept and hold tissues, cells and/or mixtures of cells (collectively referred to herein as a "biological insert"), for the purpose of maintaining the cells and/or tissue in a live state, for the purpose of growth or processing of the cells and/or tissue and/or for the purpose of transplantation of the cells and/or tissue from one region of the body to another region of the body within the same organism, and/or for the purpose of transplantation of cells and/or tissue from a donor organism to a recipient organism, even when the donor organism and the recipient organism are different species or are unrelated immunologically.

The CNTBP cage supports a strategy of transplanting into a recipient host multiple types of cells and/or tissue, which need not be immune compatible with the host, in various environments and for various applications. The invention can also provide an immune-shielded microenvironment, within a human or other host body, in which temperature, pH, oxygen levels, carbon dioxide levels, nutrient levels, metabolite levels, and levels of cytokines and other regulatory molecules (including molecules that may not be characterized) are optimum. This approach will promote or support a variety of useful biological processes that may be difficult or impossible when cells and/or tissue are maintained in culture outside the body. These processes could include maintenance of cells and/or tissue in a live state, differentiation of cells and/or tissue, de-differentiation of cells and/or tissue, enrichment of certain cell types from mixtures of cells and/or tissue, and removal of certain cell types from mixtures of cells and/or tissue. Other processes could include formation of two-dimensional or three-dimensional tissue structures from cells or mixtures of cells, including formation of nascent organs. The invention also makes possible the inclusion of scaffold structures, template structures, beads, and other structures or objects that can be placed inside a CNTBP cage (but made of materials that need not be biocompatible with the human or host body), which can be used to enhance the desired biological processes, including formation of two-dimensional and three-dimensional structures.

In some cases, the maintenance of cells and/or tissue in the cage or other biological processes may require that certain growth factors, hormones, cytokines and/or extra-cellular matrix proteins also be included in the cage. In order to prevent these growth factors, hormones, cytokines and/or extra-cellular matrix proteins from leaking out of the porous cage, it may be necessary (or desirable) to attach these growth factors, hormones, cytokines, and/or extra-cellular matrix proteins to beads, particles or other objects to be included in the cage, where the bead or particle size prevents these molecules from passing through the pores of the cage.

The cage material can be chemically modified by strategies such as: surface adsorption of various substances; covalent coupling; addition of hydrogen, oxygen, nitrogen, sulfur, halides and other chemical groups; cross-linking of materials to cause entanglement with the CNTBP; or other methods, to suit the particular application, to make the resulting CNTBP cage more suitable for a particular host type, to make the CNTBP cage more suitable for a specific location or environment within a host body, to help retain the CNTBP cage in a specified location within the host body, to select or enhance certain biological functions or processes of the cell and/or tissue contained within the CNTBP cage, and/or to avoid or minimize the need for use of immuno-suppressive drugs by the host.

In some cases, modifications of the cage material may be more appropriately carried out before construction of the cage. In other cases, modification of the cage, after its basic structure is formed, may be more appropriate, to allow specific modifications to be present only on the outside of the cage or only on the inside of the cage. In addition to cells or tissues, structures such as beads or other objects can be included within the cage, either attached to an inside wall of the cage or "free-floating," in order to enhance selected biological processes within the cage.

An immune-shield cage may also be configured to provide sensing, monitoring and/or secretion functions, for example, by controlling the porosity or another relevant parameter to permit passage of selected atoms and molecules across the cage walls.

DETAILED DESCRIPTION OF THE INVENTION

The invention uses carbon nanotube Bucky paper ("CNTBP"), a mesh of carbon nanotubes (CNTs), single-walled or multi-walled, whose thickness, density and/or porosity can be controlled in a manufacturing process. CNTBP is made entirely of carbon and is biocompatible and capable of supporting growth of some biological cells and/or tissues.

When properly prepared, a CNTBP cage will serve as a substrate for cell and/or tissue growth, and as a container for such cells (including cells, artificial cells, platelets, liposomes, proteoliposomes or other lipid-membrane-delimited structures) and/or tissue (including groups of cells, aggregates of cells, two-dimensional and three-dimensional assemblies of cells, tissue fragments, organ fragments, artificially assembled nascent organs and extra-cellular matrix elements).

Additionally, the CNTBP cage will serve as a barrier for selectively preventing invasion of unwanted biological cells and/or tissue, such as immune effector cells and blood vessels. Because it is a mesh of CNTs, CNTBP is porous and will allow oxygen, carbon dioxide, glucose, amino acids, peptides, some proteins and other molecules to diffuse relatively easily through the CNT mesh, even through multiple layers of CNT mesh. For many applications, antibodies may be permitted to cross the cage material. Because attachment of antibodies to cells, by itself, is not detrimental to the cells, if T-lymphocytes, macrophages, neutrophils or other immune effector cells cannot gain access to the antibody-coated cells For some applications, however, such as for use of the CNTBP cage to shield tissue, immune effector cells, such as T-lymphocytes, macrophages and neutrophils may already be present in the tissue. This situation may make it necessary to prevent antibodies from entering the CNTBP cage, or may make it necessary to inactivate the antibodies that enter the cage, or make it necessary to inactivate or inhibit the immune effector cells, in order to preserve the health of the CNTBP-shielded tissue.

Figure 1A:
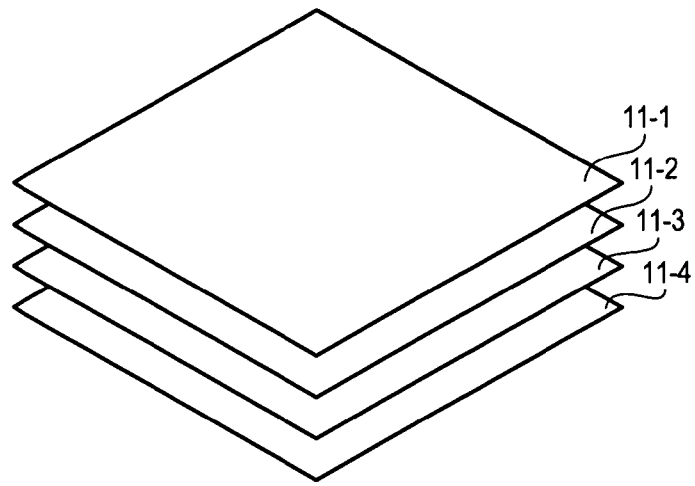
FIGS. 1A, 1B, 1C and 1D illustrate construction of a single layer or multi-layer cylindrical or toroidal cage for practice of an embodiment of the invention.
Figure 1B:
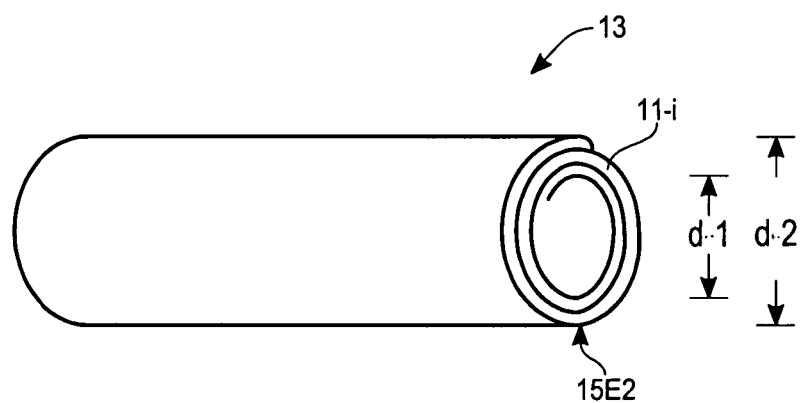
Figure 1C:
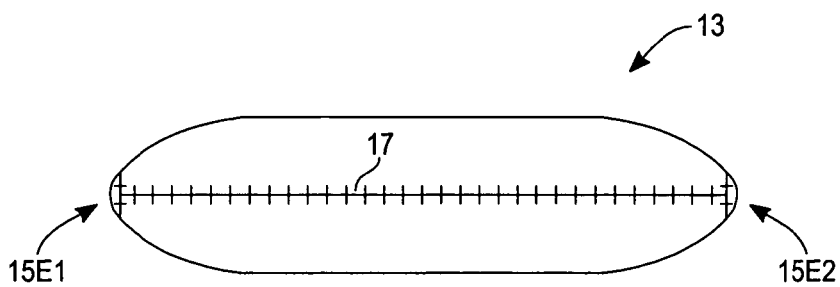

FIGS. 1A, 1B and 1C illustrate construction of a multi-layer cylindrical cage according to an embodiment of the invention. Two or more sheets of CNTBP 11-$i$ ($i$=1, ..., I) are aligned with each other in FIG. 1A and are rolled together to form a cylinder 13, with inner diameter d1 and outer diameter d2, as shown in FIG. 1B. The substance to be transplanted, processed or grown within the cylinder consisting of cells and/or tissue, including but not limited to cells, mixtures of cells, tissue, fragments of tissue, glands, fragments of glands, organs and fragments of organs) is positioned between the sheets 11-$i$ shown in FIG. 1A and/or is positioned between the sheets and within the cylinder interior shown in FIG. 1B.

In FIG. 1C, one or both ends, 15E1 and 15E2, of the cylinder 13 are sutured or otherwise stitched together to form a liquid-tight or molecule-tight end structure. Preferably, the exposed sides, 17-S-i of the rolled-up sheets are also sutured or stitched together to provide a liquid-tight or molecule-tight region for an active biological substance ABS at and adjacent to the sutures. With the ends, 15E1 and 15E2, of the cylinder 13 stitched together, the (side) walls of the resulting structure control ingress of atoms and molecules into, and egress from, the cylinder interior, including egress of an active biological substance, ABS to the ambient medium.

Figure 1D:
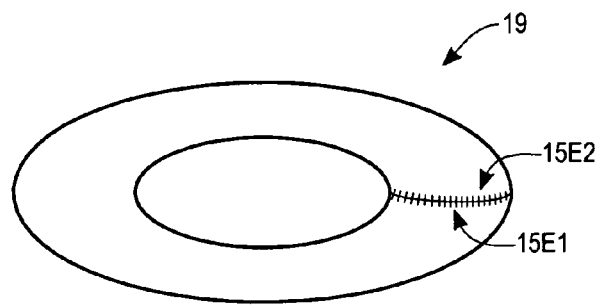

In FIG. 1D, the two ends, 15E1 and 15E2, of the (former) cylinder 13 are joined together by sutures so that the resulting structure is a torus 19. This toroidal structure has at least two advantages relative to the cylindrical structure 13 in FIG. 1C: (1) only one set (rather than two sets) of sutures is required to join or otherwise close the (former) cylinder ends; and (2) all surface regions on the torus 19 in FIG. 1D will react in approximately the same manner with the ambient medium (including, but not limited to, blood, plasma and lymph fluid) surrounding part or all of the torus, whereas the surface regions of the sutured ends, 15E1 and 15E2, of the cylinder 13 in FIG. 1C may react somewhat differently than the remainder of the cylinder surface regions.

In an alternative approach, adjacent CNTBP sheets, 11-$i$ and 11-($i$+1), are pressed together, but not tightly, so that adjacent layers of the cylinder 13 or torus 19 have a small volume of a liquid or gas, including the cells and/or tissue between them. The equivalent porosity of the cylinder or torus walls may be higher than in the first alternative so that a more diverse group of atoms and molecules is permitted ingress into, and egress from, the cylinder or torus interior. The equivalent porosity, leakage rate and/or substances that are permitted to leak are determined, in part, by the individual CNTBP sheet thicknesses, the density of the CNTs used, the number of layers presented by the rolled-up sheets 11-$i$, and the average separation distance (measured in microns) between adjacent sheets of the rolled-up cylinder sheets. This second alternative is useful where the substance in the interior of the cylinder 13 or torus 19 is used for monitoring of, or for secretion to, an environment outside the cylinder.

Figure 2A:
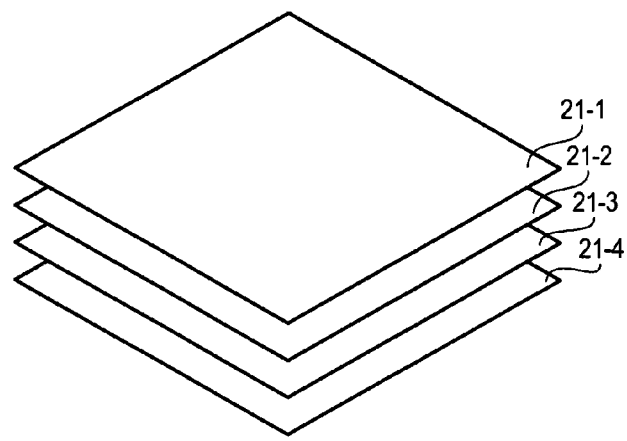
FIGS. 2A and 2B illustrate construction of a multi-sheet cage for practice of another embodiment of the invention.
Figure 2B:
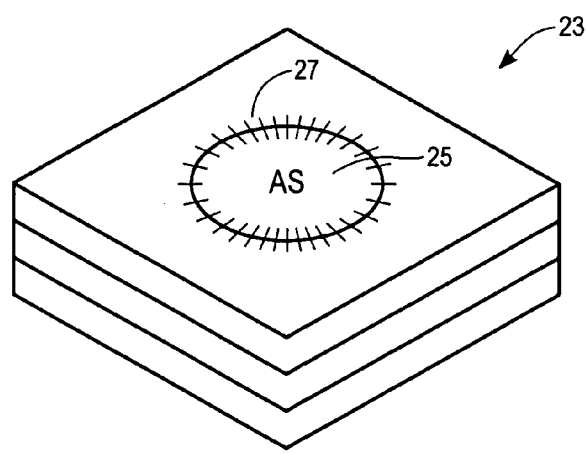

FIGS. 2A and 2B illustrate construction of a multi-sheet cage according to another embodiment of the invention. Two or more sheets of CNTBP 21-$j$ ($j=1, \ldots, J$) are aligned with each other in FIG. 2A, and the cells and/or tissue are positioned between the sheets. In FIG. 2B, the sheets are sutured or otherwise stitched together to form a sheet assembly 23 so that the cells and/or tissue cannot leak from within the sheet assembly at or adjacent to the suture region. Optionally, a central region of the sheets assembly 23 is sutured to form a pocket or pouch 25, defined by sutures 27 that holds most or all of the cells and/or tissue. A pocket may be formed by creating one or more dimples in a sheet of CNTBP.

Where the CNTBP cage is used for growth, differentiation, non-differentiation or transplantation of cells and/or tissue, the cage porosity may be selected to allow passage of some molecules and to exclude passage of other molecules. Where the CNTBP cage is used for such processing of cells and/or tissue, the cage walls preferably have a selected porosity that permits exchange of one or more selected molecules between the cage interior and the cage exterior, such as $O_2$, $CO_2$, amino acids, glucose, peptides and small proteins.

The CNTBP cage may also be used for secretion of one or more active biological substances ABS at one or more controlled rates, from the cage interior to the cage exterior. As an example, where the patient has a non-functioning or poorly functioning pancreas or thyroid, a substitute tissue, organ fragments or cells from another human, or even from another species, may be enclosed in a cage, acting as an immune shield, within the patient's body. The cage protects the non-self cells and/or tissue from an immune reaction by the patient's body but allows secretion of the desired active biological substance ABS (e.g., insulin or thyroid hormone) into the patent's body adjacent to the location of the cage.

The rate at which the active biological substance ABS is secreted into the patent's body is determined by the intrinsic sensing function of the cells and/or tissue (e.g., for insulin secreting cells and/or tissue, sensing of the presence of glucose) and is not limited by the CNTBP cage, if the CNTBP cage can be made sufficiently porous.

Figure 3:
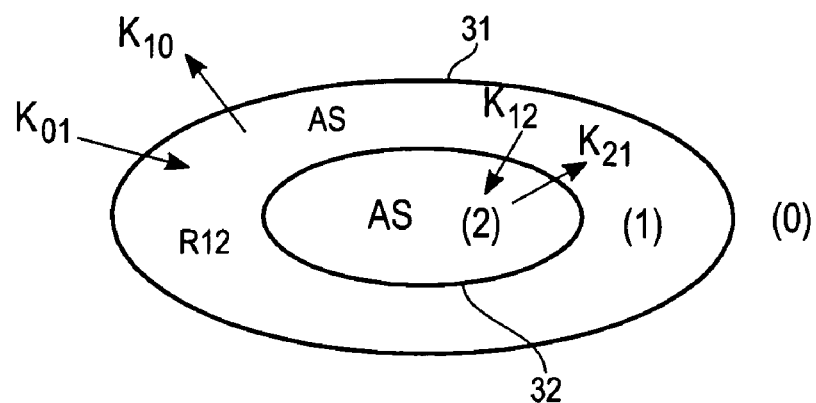
FIG. 3 illustrates a multi-cage system, according to the invention, for control of secretion rate of an active biological substance ABS.

In some cases, it may be possible to use the CNTBP cage as a delivery system to provide release of an ABS into a body by placing the ABS directly into the CNTBP cage (i.e., without using cells and/or tissue to secrete the ABS). Where an active biological substance ABS is passively released from a cage, one concern is the inevitable decrease in rate of release as the concentration of the active biological substance ABS within the cage decreases. This decrease in rate can be controlled, although not eliminated, by enclosing a second pocket or pouch 32 of the active biological substance ABS, with a second initial ABS concentration $c2(t=0)$, within a first, larger pocket or pouch 31 of the active biological substance, having an initial ABS concentration $c1(t=0)$, which is in turn immersed in an ambient medium AM, having a relatively unvarying ABS concentration $c0(t=0)$, as illustrated in FIG. 3. Preferably, the concentration values satisfy $c0(t=0)<<c1(t=0)<<c2(t=0)$. The rate constants for diffusion of the active biological substance ABS from the first pocket to the second pocket, and from the second pocket to the first pocket, have the respective values $k_{12}$ and $k_{21}$, where these two values may be equal or unequal. The rate constants for diffusion of the active biological substance ABS from the first pocket to the ambient-medium AM, and from the ambient medium to the first pocket, have the respective values $k_{10}$ and $k_{01}$, where these two values may be equal or unequal. Preferably, $k_{10}<k_{21}$. The cage material for the first pocket should be CNTBP or another material that serves as an immune shield; the cage material for the second pocket may be an immune shield material or another suitable material. This arrangement is analyzed in an Appendix. By suitable choices of ratios of the parameters, the rate of decrease of the resulting secretion rate $k_{10} \cdot c1(t)$ from the first pocket or pouch to the ambient medium AM is reduced relative to the rate of decrease that would occur if the first pouch, but not the second pouch, is present. The rate of decrease of the resulting passive release, $k_{10} \cdot c1(t)$, from the first pocket or pouch to the ambient medium AM may be further reduced by provision of N pockets, numbered $n=1, \ldots, N$ ($N \geq 3$), with pocket number $n$ being larger than and enclosing pocket number $n+1$ ($n=1, \ldots, N-1$). This approach may be used for a CNTBP cage or for a first cage made of any other material that serves as an immune shield. A stand-alone first pocket 31 can also be used for secretion, if the decrease in passive release rate for the active biological substance ABS from the pocket is not a great concern.

Figure 4:
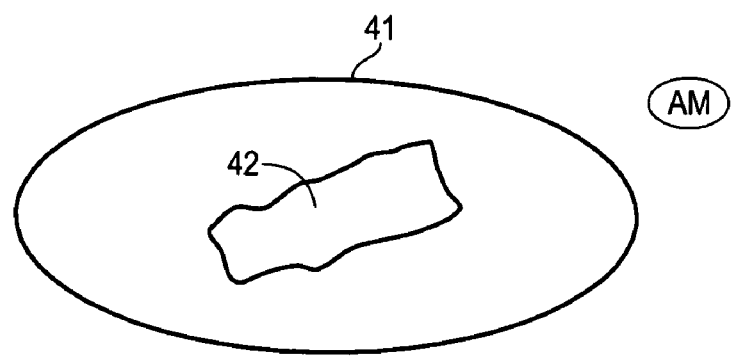
FIG. 4 illustrates use of a cage system, according to the invention, to monitor for the presence of, or concentration of, a target substance.

A CNTBP cage may also be used to sense the presence or monitor the concentration of one or more selected target substances TS in an ambient medium AM surrounding part or all of the cage 41, as illustrated in FIG. 4. In this situation, the CNTBP material is modified, as appropriate, to allow or promote transfer of the target substance across the cage material, from the ambient medium AM to the cage interior. A chemical substance or device 42, which reacts and undergoes a chemical or physical reaction, is located within the cage interior. The presence or intensity of this resulting reaction within the cage is monitored to determine the presence or the concentration of the target substance TS in the ambient medium AM.

A CNTBP cage can also support implantation into a host body of a biological insert that is genetically engineered to possess a specialized function. The activity associated with this function is controlled by an agent that can regulate specific gene expression or other specific biological activity in the biological insert and thus provide the specialized function. For some applications, the biological insert is implanted with the specialized function turned off (inactive). This insert is maintained in the host body in a live state until the specialized function is needed, at which point the biological insert is activated, for example, by administration of a chemical or biological triggering agent. When the specialized function is no longer needed, a second triggering agent is administered to deactivate the insert or expression of the specific gene or specific biological activity of the insert. Alternatively, a third triggering agent can be administered to trigger death or its equivalent in the biological insert. This approach may have particular usefulness in providing medical care to military personnel or to astronauts on long space flights, where access to conventional medical care is limited.

A CNTBP cage, acting as a quasi-immune shield, can also enclose a mechanical, electromechanical, electronic or physical medical device, which functions best when protected from exposure to or contact with one or more selected molecular substances. The medical device may provide or transform a selected chemical or a selected chemical signal, optical signal, electronic signal, electromagnetic signal, ultrasound signal, mechanical signal or other signal within the cage, for subsequent use inside or outside the cage, and may be a nano-device (with a device diameter of the order of nanometers to microns) or may be a larger device, referred to here as a macroscopic device. The CNTBP cage material may prevent passage of selected molecular substance(s) and may permit passage of other selected molecular substances, but does not interfere directly with operation of the medical device. One or more selected chemical, optical, electronic, electromagnetic, ultrasound or mechanical signals can be generated externally and passed through the CNTBP cage material to activate, deactivate, control or otherwise change the status of the medical device within the cage. Apart from replacement of mis-functioning or non-functioning medical devices and their respective cages from time to time, no further actions are required, other than passage of the selected signal, or sequence of signals, through the cage material.

Activation of the biological insert can be implemented, for example, using one or more optical or other suitable signals to "awaken" the specialized function of the insert. The optical signal may have one or more wavelengths in the visible, infrared or microwave regions, depending upon the distance of the CNTBP cage from an exposed portion of the host body through which the optical signal enters. A timed sequence of non-simultaneous optical signals can be used to raise the energy level of a particular electron or group of electrons to a selected level(s) at which activation occurs. An ultraviolet optical signal can be used for such purpose, if the CNTBP cage is located close to an exposed surface of the body, for example, in a skin layer. Until such activation occurs, the biological insert within the CNTBP cage is effectively inert. Delivery of one or more selected optical signals can also be used to deactivate an already-active biological insert so that the biological insert can be switched on and off, depending upon need.

Transfer characteristics across a meshwork of CNTBP material can also be modified by inclusion and/or attachment of selected functional groups (e.g., groups involving H, O, N, S, F, Cl, Br, I, a protein, a peptide, a polypeptide, a growth factor, a cytokine, a nucleic acid and/or a nucleic acid polymer) to the CNTs before the CNTBP is prepared. Some of these functional groups may serve as "markers" in a manner similar to biological markers on a cell membrane, thereby selectively controlling the chemical substances that are transferred across a cage wall and/or the rate at which such transfer occurs.

CNTBP Preparation. In one approach, the CNTBP used in the invention is prepared from crude preparations of single wall carbon nanotubes ("SWCNTs") synthesized by a laser ablation technique, available from commercial sources. Other preparations of SWCNTs or multiple wall carbon nanotubes ("MWCNTs"), such as those synthesized by the well known HiPCO technique (a high pressure process using carbon monoxide) are also acceptable. The crude preparation is first purified by refluxing in nitric acid for 160 hours and the resulting product is centrifuged. A pellet (resulting from centrifugation) is suspended in potassium hydroxide solution (pH≈10), then washed twice by centrifugation and re-suspension. The purified CNTs are washed twice in distilled water, using centrifugation and resuspension. The purified CNTs are re-suspended in distilled water, then mechanically formed into Bucky paper by removal of water by vacuum filtration over a cellulose filter or similar filter. Portions of the CNTs incorporated in the Bucky paper produced here may be "bundled", or partially or fully aligned, due to liquid flow through the mesh of CNTs, which may provide a higher than normal density of CNTs in an array.

Figure 5:
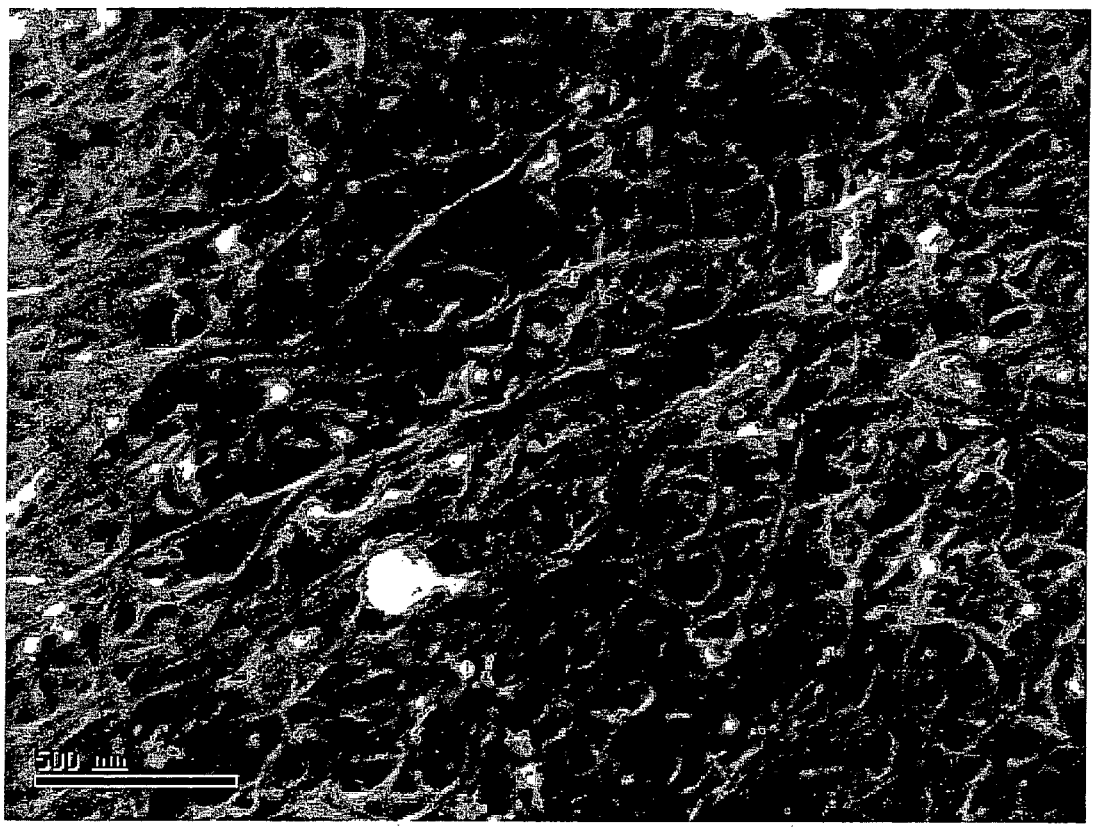
FIG. 5 is a scanning electron microphotograph (SEM) image of a piece of CNTBP.

The CNTBP used in the invention preferably has a thickness in the range of 1–100 μm and an area density in the range of 420–1500 μgm/cm$^2$. FIG. 5 is a scanning electron microphotograph (SEM) image of a Bucky paper scrap after fabrication.

Separate procedures are optionally provided for generating and controlling patterns or densities of growth of an array of SWCNTs or MWNTs, with a CNT length that depends upon the structure involved. A CNT can be grown with a length between about 1 μm and 200 μm, or longer if desired. However, control of the length of the CNTs may not be important for CNTBP applications. The CNTBP support material will preferably form a mesh or mat. The mesh thickness h(mesh) and mesh density partly determine the CNTBP porosity. A mesh density range of $4 \times 10^6 - 6 \times 10^{10}$ cm$^2$, corresponding to a range d=40 nm–5 μm for average nearest neighbor center-to-center separation distance is produced where a substrate is not used for CNT growth. Use of a higher Bucky paper average thickness h may require use of a higher separation distance d, to preserve similar Bucky paper behavior.

Unique features of this invention include a material (CNTBP) that has not yet been used extensively in biological applications, the biocompatibility of the material, the potential to permit or block the passage of various substances across the CNTBP by controlling the porosity of the CNTBP, the ease of use and variety of shapes into which the material can be shaped, and an ability to control the dimensions of a cage made from the material. The invention provides a micro-environment in which growth, promotion of or suppression of cell differentiation, transplantation of cells and tissues, as well as secretion, sensing and monitoring of chemical substances present can be performed, without the need for, or with limited need for, use of immunosuppressive drugs or other special precautions.

Appendix

In the structure shown in FIG. 3, a first envelope 31 is immersed in an ambient medium AM, referred to with the index "0," having an initial concentration c0($t=0$) of a selected active biological substance (ABS) The first envelope 31 is constructed of carbon nanotube Bucky paper (CNTBP) and contains the ABS with an initial concentration of c1($t=0$). A second envelope 32, constructed of CNTBP or another selected material, is wholly contained within the first envelope 31 and contains the ABS with an initial concentration of c2($t=0$). Transfer of the ABS from between the second envelope and the region R12 within the first envelope that is outside the second envelope, and between the region R12 and the ambient medium AM are approximately described by the equations $$d(c1 \cdot V1)/dt = -\{(k_{12} \cdot S_{12})/V1 + (k_{10} \cdot S_{10})/V1\}(c1 \cdot V1) + \{(k_{21} \cdot S_{12})/V2\}(c2 \cdot V2) + \{(k_{01} \cdot S_{10})/V0\}(c0 \cdot V0), \quad \text{(A-1)}$$

$$d(c2 \cdot V2)/dt = -\{(k_{21} \cdot S_{12})/V2\}(c2 \cdot V2) + \{(k_{12} \cdot S_{12})/V1\}(c1 \cdot V1), \quad \text{(A-2)}$$

where c0, c1 and c2 are concentrations (in units of mm$^{-3}$) of the ABS in the ambient medium, in the region R12 and in the second envelope interior, respectively, $k_{21}$ and $k_{12}$ are diffusion rate constants for transfer of the ABS from the second envelope interior to the region R12 and from the region R12 to the second envelope interior, $k_{01}$ and $k_{10}$ are diffusion rate constants for transfer of the ABS from the ambient medium to the region R12 and from the region R12 to the ambient medium, V0 is the ambient medium volume, V1 is the volume of the region R12, V2 is the volume of the second envelope interior, S10 is the surface area of the first envelope (between the ambient medium and the region R12), and S12 is the surface area of the second envelope. Introducing the parameters $$\alpha = (k_{21} \cdot S_{12})/V2,$$

$$\beta = (k_{12} \cdot S_{12})/V1,$$

$$\chi = (k_{01} \cdot S_{10})/V0, \quad \text{(A-3)}$$

$$\delta = (k_{10} \cdot S_{10})/V1,$$

$$\kappa = \{-\beta - [\beta^2 + 4\alpha]^{1/2}\}/2 (<0),$$

the physically realistic and interesting solution of the coupled equations (A-1) and (A-2) becomes $$c2(t) \cdot V2 = \{c2(0) \cdot V2 - \chi \cdot c(0) \cdot V0/(\alpha 2 - \alpha \cdot \beta - \alpha)\} \exp(\kappa t) + \chi \cdot c(0) \cdot V0/(\alpha 2 - \alpha \cdot \beta - \alpha)\} \exp(\alpha t), \quad \text{(A-4)}$$

$$c1(t) \cdot V1 = \{d(c2 \cdot V2)/dt + \alpha \cdot c2(t) \cdot V2\}/\beta, \quad \text{(A-5)}$$

It is assumed here that c0($t=0$)<<c1($t=0$)<<c2($t=0$).

Several observations can be made from Eqs. (A-4) and (A-5). First, the magnitude of the exponential decrease with time of the concentration variable c1(t) is less than the magnitude of the exponential decrease of that variable that would occur if the second envelope were absent. Second, the concentration variable c1(t) decreases toward a smaller positive value. Third, the surface area S12 is an important parameter in moderating the magnitude of the exponential decrease of the concentration variable c1(t). With the second envelope present, the decrease in the net exchange rate of the ABS, $$(k_{10} \cdot S_{10})/V1\}(c1 \cdot V1) - (k_{01} \cdot S_{10})/V0\}(c0 \cdot V0),$$

across the first envelope surface is reduced, and the exchange rate is maintained at a value closer to a constant value.

What is claimed is:

1. A system for enclosing a biological tissues or group of cells for positioning within an ambient medium, the system comprising:
   a cage or envelope of a cage material that includes primarily carbon nanotube Bucky paper ("CNTBP"), the cage having at least one of a cage thickness in a range 1–100 μm and a cage area density in a range of 420–1500 μgm/cm$^2$, where the cage encloses at least one of a biological tissue or a group of cells (referred to herein as a "biological insert") and an interior of the cage is substantially isolated from an ambient medium surrounding the cage, except for transport at least one species of molecule between the cage interior and the ambient medium.

2. The system of claim 1, wherein said cage is used to grow said biological insert without provoking a substantial immunological response from said ambient medium.

3. The system of claim 1, wherein said cage is used to place cells derived from a cell culture into a biological host without provoking a substantial immunological response from the biological host.

4. The system of claim 1, wherein said cage is used to place at least one of a bacterial cell, a yeast cell, a mammalian cell and a non-mammalian cell into a biological host without provoking a substantial immunological response from the biological host.

5. The system of claim 1, wherein said biological insert includes at least one cell that is capable of cell differentiation and said cage promotes cell differentiation by the at least one cell without provoking a substantial immunological response from said ambient medium.

6. The system of claim 1, wherein said cage is modified by addition of an active biological substance to said interior of said cage.

7. The system of claim 6, wherein said active biological substance is selected to be at least one of a protein, a peptide, a polypeptide, a growth factor, a cytokine, a nucleic acid and a nucleic acid polymer.

8. The system of claim 6, wherein said active biological substance is added to said cage interior by at least one of: non-specific adsorption, covalent coupling and chemical cross-linking so that said active biological substance becomes entangled with said CNTBP cage material.

9. The system of claim 6, wherein said active biological substance is added to said cage interior by attachment to a bead so that the bead and said attached active biological substance cannot be transported from inside said cage to outside said cage.

10. The system of claim 6, wherein said cage interior, modified by said addition of said active biological substance enhances at least one process of: growth, differentiation, de-differentiation, assembly into a two-dimensional cell structure, and assembly into a three-dimensional cell structure, of said biological insert.

11. The system of claim 1, wherein said cage is modified by at least one of covalent attachment of an active biological substance to an exterior of said cage and adsorption of the active biological substance to the exterior of said cage.

12. The system of claim 11, wherein said active biological substance is selected to be at least one of a protein, a peptide, a polypeptide, a growth factor, a cytokine, a nucleic acid and a nucleic acid polymer.

13. The system of claim 11, wherein said cage exterior, modified by said addition of said active biological substance enhances immune shielding by said cage.

14. The system of claim 1, wherein said biological insert includes at least one cell that is capable of cell differentiation and said cage suppresses cell differentiation by the at least one cell without provoking a substantial immunological response from a biological host that contains said cage.

15. The system of claim 1, wherein said cage is used to transplant said biological insert from a first organism to a second organism without provoking a substantial immunological response from at least one of the first organism and the second organism.

16. The system of claim 1, wherein said cage is used to transplant said biological insert from a first region of a host body to a second region of the host body without provoking a substantial immunological response from the host body.

17. The system of claim 1, wherein said cage has at least two adjacent layers of said CNTBP material and substantially has a shape drawn from a class of cage shapes consisting of a cylinder, a torus and a multiple-sheet structure.

18. The system of claim 1, wherein said cage is chemically modified by addition of at least one of a hydride, a nitride, an oxide, a halide, a sulfide, a protein, and a peptide to said cage material.

19. A system for providing secretion of an active biological substance into an ambient medium, the system comprising:
an active biological substance enclosed in a cage or envelope of a cage material that includes primarily carbon nanotube Bucky paper ("CNTBP"), having at least one of a cage thickness in a range 1–100 μm and a cage area density in a range of 420–1500 μg/cm$^2$, where an interior of the cage is substantially isolated from an ambient medium located in an exterior of the cage, except for transport of molecules of at least one species between the cage interior and the cage exterior, and where the active biological substance has a positive rate of transfer across the cage material from the cage interior to the cage exterior.

20. The system of claim 19, wherein said cage further encloses at least one of a thyroid tissue or portion of a thyroid gland and said cage permits transfer of a thyroid hormone or other composition that includes iodine from inside said cage to outside said cage.

21. The system of claim 19, wherein said cage further encloses at least one of a pancreas tissue or portion of a pancreas gland and said cage permits transfer of a pancreas hormone or other composition that includes insulin from inside said cage to outside said cage.

22. The system of claim 19, wherein said cage is chemically modified by addition of at least one of a protein, a peptide and a molecule including at least one of a hydrogen atom, an oxygen atom, a nitrogen atom, a sulfur atom, a fluorine atom, a chlorine atom, a bromine atom and an iodine atom to said cage material.

23. A method for providing secretion of an active biological substance into an ambient medium, the method comprising:

enclosing at least one of a tissue and a group of cells (referred to herein as a "biological insert"), having a capability of secreting a chemical and having an insert first concentration, in a first cage or envelope of a first cage material that includes primarily carbon nanotube Bucky paper ("CNTBP"), having at least one of a cage thickness in a range 1–100 μm and a cage area density in a range of 420–1500 $\mu gm/cm^2$, where the biological insert has a positive rate of transfer across the first cage material from a first cage interior to a first cage exterior; and enclosing a second biological insert, having an insert second concentration, in a second cage or envelope of a second cage material, having a second cage thickness, where an interior of the second cage is contained within the first cage and where the second biological insert within the second cage has a positive rate of transfer across the second cage material from a second cage interior to the first cage interior.

24. The method of claim 23, further comprising enclosing within said second cage at least one of a thyroid tissue and a portion of a thyroid gland.

25. The method of claim 23, further comprising enclosing within said second cage at least one of a pancreas tissue and a portion of a pancreas gland.

26. The method of claim 23, further comprising chemically modifying said cage by addition of at least one of a protein, a peptide and a molecule including at least one of a hydrogen atom an oxygen atom, a nitrogen atom, a sulfur atom, a fluorine atom, a chlorine atom, a bromine atom and an iodine atom to said cage material.

27. A method for monitoring at least one of presence and concentration of an active biological substance in an ambient medium, the method comprising:

enclosing a monitoring substance, which reacts with a monitored substance and undergoes at least one of a chemical change and a physical change, in a cage or envelope of a cage material that includes primarily carbon nanotube Bucky paper ("CNTBP"), the cage having at least one of a cage thickness in a range 1–100 μm and a cage area density in a range of 420–1500 $\mu gm/cm^2$, where an interior of the cage is substantially isolated from an ambient medium located in an exterior of the cage and where the monitored substance has a positive rate of transfer across the cage material between a cage exterior and a cage interior; and when the monitoring substance undergoes at least one of the chemical change and the physical change, the system interprets this condition to indicate that the monitored substance is present in the ambient medium.

28. The method of claim 27, further comprising chemically modifying said cage by addition of at least one of a protein, a peptide and a molecule including at least one of a hydrogen atom, an oxygen atom, a nitrogen atom, a sulfur atom, a fluorine atom, a chlorine atom, a bromine atom and an iodine atom to said cage material.

29. A method for controlling activity of a biological tissue or group of cells in a host body, the method comprising:

enclosing a biological tissue or group of cells (referred to herein as a "biological insert") that is initially in an inactive state, in a cage or envelope of a cage material that includes primarily carbon nanotube Bucky paper ("CNTBP"), the cage having at least one of a cage thickness in a range 1–100 μm and a cage area density in a range of 420–1500 $\mu gm/cm^2$, where an interior of the cage is substantially isolated from an ambient medium located in an exterior of the cage; and at a first time, administering a triggering agent to at least one of the ambient medium and the cage interior to activate the biological insert and to permit at least part of the activated biological insert to secrete an active biological substance within the cage.

30. The method of claim 29, further comprising administering, at a second time subsequent to said first time, a second triggering agent to at least one of said ambient medium and said cage interior to deactivate said activated biological insert that is located in at least one of said cage interior and said ambient medium.

31. The method of claim 29, further comprising chemically modifying said cage by addition of at least one of a protein, a peptide and a molecule including at least one of a hydrogen atom, an oxygen atom, a nitrogen atom, a sulfur atom, a fluorine atom, a chlorine atom, a bromine atom and an iodine atom to said cage material.

32. A method for providing a medical device within a host body, the method comprising:
    enclosing a medical device in a cage or envelope of a cage material that includes primarily carbon nanotube Bucky paper ("CNTBP"), having at least one of a cage thickness in a range 1–100 µm and a cage area density in a range of 420–1500 µgm/cm², where an interior of the cage is substantially isolated from an ambient medium surrounding the cage, except for transport of a molecule of at least one species between the cage interior and the ambient medium where the cage material acts as a shield to prevent molecules, other than the at least one species molecule, in the ambient medium from contacting the device;
    when the medical device is initially inactive, providing a medical device activation signal that activates the device at an activation time; and
    when the medical device is initially active, providing a medical device inactivation signal that inactivates the device at an inactivation time.

33. The method of claim 32, further comprising selecting said medical device to be a nano-device that provides or transforms at least one of a chemical and a signal within said cage.

34. The method of claim 32, further comprising selecting said medical device to be a macroscopic device that provides or transforms at least one of a chemical and a signal within said cage.

35. The method of claim 32, further comprising providing at least one of said activation signal and said inactivation signal as at least one of a chemical signal, an optical signal, an electronic signal, an electromagnetic signal, an ultrasound signal and a mechanical signal that is initially produced outside said cage, passes through said cage material, and interacts with said medical device.

36. The method of claim 32, further comprising:
    when said medical device is initially active, providing a medical device control signal that changes at least one operating parameter for said medical device at a control time.

37. The method of claim 36, further comprising providing at least one of said activation signal and said inactivation signal as at least one of a chemical signal, an optical signal, an electronic signal, an electromagnetic signal, an ultrasound signal and a mechanical signal that is initially produced outside said cage, passes through said cage material, and interacts with said medical device.

38. The system of claim 6, wherein said active biological substance is produced by said biological insert within said cage.

39. The system of claim 38, wherein said active biological substance enhances at least one of the following processes associated with said biological insert: growth, differentiation, de-differentiation, assembly into a two-dimensional cell structure, and assembly into a three-dimensional cell structure.

40. The system of claim 1, wherein said cage is modified by at least one of covalent attachment an active biological substance to an exterior of said cage and adsorption of the active biological substance to the interior of said cage.

41. The system of claim 1, wherein said biological insert includes at least one cell that is capable of cell differentiation and said cage promotes cell differentiation by the at least one cell without provoking a substantial immunological response from a biological host that contains said cage.

42. The method of claim 29, further comprising choosing said active biological substance from the group of substances consisting of insulin, cytokines and biological response modifiers.

* * * * *